US 6,692,694 B1

(12) United States Patent
Curry et al.

(10) Patent No.: US 6,692,694 B1
(45) Date of Patent: Feb. 17, 2004

(54) METHOD AND APPARATUS FOR PHOTOSENSITIZED ULTRAVIOLET DECONTAMINATION OF SURFACES AND AEROSOL CLOUDS

(75) Inventors: Randy Dale Curry, Columbia, MO (US); Jeffry Golden, Laurel, MD (US)

(73) Assignee: Clean Earth Technologies, LLC, St. Louis, MO (US)

( * ) Notice: Subject to any disclaimer, the term of this patent is extended or adjusted under 35 U.S.C. 154(b) by 0 days.

(21) Appl. No.: 09/436,058

(22) Filed: Nov. 8, 1999

Related U.S. Application Data

(60) Provisional application No. 60/107,617, filed on Nov. 9, 1998.

(51) Int. Cl.[7] ............................................. A61L 9/015
(52) U.S. Cl. ........................ 422/28; 422/1; 422/22; 422/74; 422/186.3
(58) Field of Search .................... 422/1, 22, 24, 422/28, 186.3; 53/167

(56) References Cited

U.S. PATENT DOCUMENTS

| | | | |
|---|---|---|---|
| 4,014,158 A | | 3/1977 | Rausing |
| 4,051,058 A | | 9/1977 | Bowing et al. |
| 4,051,059 A | | 9/1977 | Bowing et al. |
| 4,366,125 A | * | 12/1982 | Kodera et al. ............... 422/295 |
| 4,424,189 A | | 1/1984 | Hick |
| 4,464,336 A | | 8/1984 | Hiramoto |
| 4,518,585 A | * | 5/1985 | Greene et al. ............... 424/130 |
| 4,680,163 A | * | 7/1987 | Blidschun et al. ............ 422/28 |
| 4,866,282 A | | 9/1989 | Miripol et al. |
| 4,867,796 A | * | 9/1989 | Asmus et al. ................... 131/1 |
| 4,871,559 A | | 10/1989 | Dunn et al. |
| 5,114,670 A | * | 5/1992 | Duffey .......................... 422/24 |
| 5,256,379 A | * | 10/1993 | Deloach ................. 422/186.3 |
| 5,658,530 A | | 8/1997 | Dunn |
| 5,744,094 A | * | 4/1998 | Castberg et al. .............. 422/24 |
| 5,768,853 A | | 6/1998 | Bushnell et al. |
| 5,786,598 A | | 7/1998 | Clark et al. |
| 5,840,343 A | * | 11/1998 | Hall, II et al. ............... 424/616 |
| 5,857,309 A | * | 1/1999 | Cicha et al. .................... 53/167 |
| 5,900,211 A | | 5/1999 | Dunn et al. |
| 5,925,885 A | | 7/1999 | Clark et al. |
| 6,183,807 B1 | * | 2/2001 | Gutzmann et al. .......... 426/652 |

FOREIGN PATENT DOCUMENTS

WO     WO 93/00815     *   1/1993

OTHER PUBLICATIONS

The Zero Tol Product Information Sheet.
Bayliss et al., The Combined Effect of Hydrogen Peroxide and Ultraviolet Irradiation on Bacterial Spores, *Journal of Applied Bacteriology* 47:263–269 (1979).
Bayliss et al., The Effect of Hydrogen Peroxide and Ultraviolet irradiation on Non–sporing Bacteria, *Journal of Applied Bacteriology* 48:417–422 (1980).
Bayliss et al., Resistance of *Serratia marcescens* to Hydrogen Peroxide, *Journal of Applied Bacteriology* 50:131–137 (1981).
Bayliss et al., Resistance and Structure of Spores of *Bacillus subtilis*, *Journal of Applied Bacteriology* 50:379–390 (1981).

* cited by examiner

*Primary Examiner*—Robert J. Warden, Sr.
*Assistant Examiner*—Sean Conley
(74) *Attorney, Agent, or Firm*—Husch & Eppenberger LLC; Grant D. Kang

(57) ABSTRACT

A method of deactivating chemical contaminants and biological agents from a target surface by aerosol spraying the target surface with a electrostatically charged, photosensitizer solution, and then illuminating the surface with ultraviolet light.

8 Claims, 13 Drawing Sheets

Aerosol Agents

752

Aerosol Agents Clump at Surface

UV

750 Decontamination Aerosol
Embedded Charge

754

Aerosol Agents Clump at Surface of the Decontamination Agent

UV

Embedded Charge $H_2O_2$

OH

Decontamination Agent Containing Hydrogen Peroxide or Ferrioxalate

Fig. 10

METHOD AND APPARATUS FOR PHOTOSENSITIZED ULTRAVIOLET DECONTAMINATION OF SURFACES AND AEROSOL CLOUDS

This application claims priority of U.S. provisional patent application No. 60/107,617, filed Nov. 9, 1998.

FIELD OF THE INVENTION

This invention relates to decontamination methods and apparatus, and in particular to methods of and apparatus for using photosensitizers and light to treat chemical and/or biological contaminants on surfaces and in aerosol clouds.

BACKGROUND OF THE INVENTION

Biological decontamination is the destruction of microorganisms, and pathogens, such as bacteria, both vegetative and sporulative, bacterial spores, viruses, mycoplasma, protozoans, oocysts, and toxins. Chemical contamination is the destruction of chemical contaminants, pesticides, chemical warefare agents, and other toxic substances. Current methods of decontamination and disinfection of surfaces include chemical washing, fumigation, heat treatment, and irradiation. Chemical washing includes washing the surface with anything from simple soap and water, to sodium hypochlorite (bleach), DS-2, hydrogen peroxide, alkali, hexachlorophene, and quaternary amines. Fumigation includes exposing an object or surface of an object to a fumigant. A common fumigant is ethylene oxide (EtO), a flammable, carcinogenic/mutagenic compound; another is ozone, a toxic gas. Heat treatment includes wet and dry autoclaving, including steam heating, and high temperature heating in an oven. Heat treatment is sometimes augmented with substances that reduce the heat resistance of bacterial spores, such as ethylene oxide, hydrogen peroxide, garlic oil, nisin, subtilin methyl ester, and others. For example, it is known in the art that microwave heating combined with application of hydrogen peroxide is an efficacious bactericidal treatment. Irradiation, such as with ionizing radiation is also used to alter chemical contamination and/or to disinfect. Ionizing radiation is most commonly performed by exposure to gamma rays from a radioactive source, or by exposure to x-rays or electrons from an electron accelerator.

Each of these methods has proven to be effective for certain situations, but each has certain problems. Chemical washing in the field is environmentally unsound because it results in distribution of toxic chemical washes. The use of fumigants, including ethylene oxide, has associated occupational and operational hazards. Heat treatment in autoclaves is not practical for large objects and cannot be used for decontaminating people, or for equipment that would be harmed by heat. Irradiation requires either a radioactive source or an accelerator, which are generally cumbersome and require either substantial shielding or 'standoff' distance for safety for people and animals. Thus, for reasons of cost, portability, environmental impact, or safety, the existing methods have limited practicality and attractiveness.

Surface cleaning with UV light has been used in the preparation of microelectronic materials and devices, but has limited effect on destroying chemical contamination. Reactive gas can be used in combination with UV light, but this process must be performed in a controlled environment, either a high average power laser UV source or high flow gas jet must be used to achieve satisfactory cleaning rates.

UV light is also used in disinfection processes, but typically requires enormous fluence and exposure (absorbed energy per unit area). See, for example, Clark et al., U.S. Pat. Nos. 5,786,598 and 5,925,885, Dunn, U.S. Pat. No. 4,871,559, Hiramoto, U.S. Pat. No. 4,464,336, and Busnell, U.S. Pat. No. 5,768,853, incorporated herein by reference. This requires multiple UV light sources and long exposure times which are not practical for many applications such as decontamination or disinfection of people, equipment, spaces that must be returned to activity or use as quickly as possible. Although the use of more powerful light sources can reduce exposure times, high exposure to UV light can cause degradation of many materials and, in the case of people, harmful biological effects such as erythema and burn. UV light reflected off some surfaces may pose a hazard to people and property nearby.

Finally, higher average power and higher fluence sources generally have lower efficiencies, increasing power consumption and generating excess heat.

UV light has also been used in conjunction with catalysts for decontaminating water and stack gases, and used in connection with ozone and chlorination process, but these methods are not applicable to surface decontamination. See, for example, Dunn, U.S. Pat. Nos. 5,658,530 and 5,900,211, incorporated herein by reference.

Hydrogen peroxide compositions have been used as disinfectants. See Bowing et al., U.S. Pat. Nos. 4,051,058 and 4,051,059, incorporated herein by reference. UV light and hydrogen peroxide have been used in the sterilization of cartons. See Bayliss and Waites, "The Combined Effect of Hydrogen Peroxide and Ultraviolet Irradiation on Bacterial Spores" 47 Journal of Applied Bacteriology 263–269 (1979), and Bayliss and Waites "The Effect of Hydrogen Peroxide and Ultraviolet Irradiation on Non-sporing Bacteria" 48 Journal of Applied Bacteriology 417–422 (1980), Bayliss and Waites, "Resistance of Serratia marcescens to Hydrogen Peroxide" 50 Journal of Applied Bacteriology 131–137 (1981), and Bayliss and Waites, "Resistance of Structure of Spores of Bacillus subtilis" 50 Journal of Applied Bacteriology 379–390 (1981), incorporated herein by reference. In one method hydrogen peroxide vapor or mist is applied within an enclosed volume and subsequent exposure to UV light. In another method a solution of hydrogen peroxide having a concentration that is less than 10%, is applied and UV light with wavelength less than 325 nm, is applied. Hydrogen peroxide and UV light is also used in the treatment of wastewater.

All of these previously applied methods and the apparatus associated with these methods are not well suited for decontamination or disinfection in a relatively unconfined or uncontrolled environment or situation. Examples of such situations include the decontamination/disinfection of surfaces of people, their garments, equipment, and occupiable spaces as part of the consequence management of a natural disaster, an industrial accident, a transportation accident, criminal violence, terrorist attack, or in a military situation, e.g., chemical or biological warfare. Another example of a relatively uncontrolled environment is a drifting cloud of hazardous chemical agent or infectious biological agent. Such a cloud might occur as a result of the any of the above situations.

There are many additional situations in which a method and apparatus that can be rapidly deployed or used on an occasional basis in variable environmental conditions, would be beneficial. Applications for such a system include cleaning and disinfection of surfaces in medical, food preparation, and pharmaceutical facilities and the decontamination and disinfection of personnel and equipment following exposure to military chemical and biological warfare agents as part of the demilitarization of such materials. Other applications include the disinfection of medical implements, medical waste containers, and medical waste treatment equipment. There are many additional situations in which benefits would be realized by a method and apparatus that can be rapidly deployed or used on an occasional basis or with variable environmental conditions.

SUMMARY OF THE INVENTION

Generally according to the process of this invention, a photosensitizer is applied to a contaminated surface or to a contaminated aerosol cloud, and the surface or the cloud is illuminated. The photosensitizer is preferably applied as an aerosol spray. The photosensitized contaminants or pathogens on the surface or in the cloud are preferably illuminated with ultraviolet (UV) light of sufficient intensity to cause photochemical destruction or deactivation of the contaminants or pathogens.

The delivery of the photosensitizer can be targeted by electrically charging the photosensitizer as it is applied. The amount of UV light energy can be controlled by monitoring the UV light exposure received by the surface being illuminated or by monitoring the UV light intensity at a known distance from the UV light source, and using the time integrated signal from the monitoring as a feedback signal.

The process can be conducted in a shielded area to protect persons and objects in the surrounding environment from exposure to the photosensitizer and the UV light, and the airflow within the shielded area can be controlled so that persons and objects in the surrounding environment are not contaminated. The shield can be electrically charged to collect and thereby contain excess photosensitizer.

Thus the invention provides a process for the photosensitized decontamination or disinfection of surfaces of an object or an aerosol cloud. A photosensitizer can be quickly, easily and inexpensively disbursed on a surface into an aerosol cloud. The surface or the aerosol cloud is illuminated with UV light. UV exposure or directed intensity can be monitored and the duration of illumination on the average power of the emitted UV light can be adjusted to obtain the desired time integrated exposure. If needed, additional photosensitizer during or between periods of UV illumination. Finally, the remaining products of the illuminated photosensitizer on the surface or in the cloud can be neutralized on removal. A shield can provide a means of protecting nearby objects, the environment, and persons from unwanted exposure to the sprayed photosensitizer or the emitted light.

These and other features and advantages of the present invention will become apparent from the following detailed description, which taken in conjunction with the annexed drawings, discloses the preferred embodiments of the present invention.

BRIEF DESCRIPTION OF THE DRAWINGS

FIG. 10 is a schematic drawing of the clumping of aerosol chemical or biological agents at the surface of a photosensitizer aerosol droplet or particle because of electric charges;

DETAILED DESCRIPTION OF THE INVENTION

Figure 1:
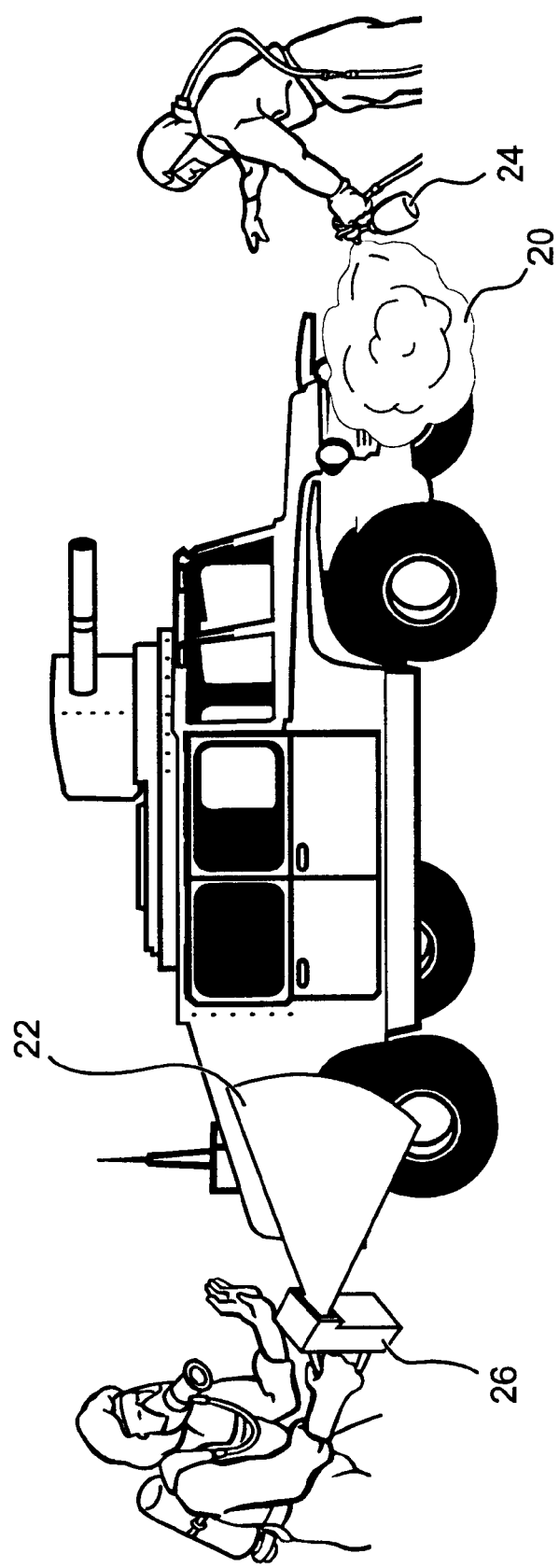
FIG. 1 is a schematic diagram of a process for decontaminating a surface in accordance with the principles of this invention.

A process for decontaminating surfaces in accordance with the principles of the present invention is illustrated schematically in FIG. 1. The process is adaptable for treating chemical and/or biological contamination of a surface. Generally, a photosensitizer is applied to the surface, preferably as an aerosol spray. The surface is then illuminated, preferably with ultraviolet light, with sufficient intensity (power per unit area) to effect decontamination. This decontamination can result from the photodecomposition of the chemical contaminants or alteration of critical biological molecules or structures of the pathogens, and/or result in chemical reaction with the products of photochemical reactions to effect the decontamination or deactivation.

Additional photosensitizer may be applied during the illumination so that a sufficient quantity of photosensitizer is available to contact the contaminants and/or pathogens, and thus the photosensitizer-enhanced reactions proceed efficiently, and are not limited by an inadequate concentration of the photosensitizer.

According to one aspect of this invention, the photosensitizer can be electrostatically charged as it is sprayed as an aerosol, hereinafter "electro-sprayed", to promote the adherence of the photosensitizer to the surface to be treated. For conducting or semiconducting targets, or dielectric targets that are backed by conductors or have conductors within their structure, the charged particles resulting from the electro-spraying will be attracted to, and adhere to, the surface to be treated.

The process of this invention is particularly suited for the decontamination or disinfection of surfaces pertaining to people, their garments, equipment, and occupiable spaces as part of the consequence management of a natural disaster, an industrial accident, a transportation accident, criminal violence, terrorist attack, or in a military situation, e.g., chemical or biological warfare.

As shown in FIG. 1, photosensitizer 20 is applied to a surface, such as the surface of a vehicle 22, in the form of an aerosol spray, using sprayer unit 24. While as shown and described herein the surface is the surface of a vehicle, the invention is not so limited and the methods and apparatus of this invention may be used in treating any surface contaminated by a chemical or biological agent which is accessible to the aerosol or other delivery of the photosensitizer and UV illumination. The sprayer 24 may be a hand-operated pump sprayer, or other suitable device. The selection of the photosensitizer depends upon whether photooxidative, photocytotoxic or photodynamic reactions are desired for their microbicidal or chemical decontamination effect. For broad spectrum microbicidal effect, photooxidative photosensitive effects are preferred. Suitable photosensitizers include mixtures of peroxy compounds, including anything that has an —OH or an —OOH group, including hydrogen peroxide, paracetic acid, hydrogen peroxide and paracetic acid, perpropioniac acid, propionic acid, and mixtures thereof. One suitable photosensitizer is an aqueous solution containing about 0.1% to about 10% hydrogen peroxide; however, the inventors have found superior results with an aqueous solution containing about 0.1% to about 10% hydrogen peroxide and from about 0.01% to about 1% peracetic acid. ZEROTOL™, available from Bio-Safe System, Inc., or RENALIN™ available from Minntech Corp. are suitable photosensitizers. A surfactant may be added to the photosensitizer to aid in the dispersion and coating of the surface with the photosensitizer. The selection of the surfactant depends upon its action as a wetting agent and its non-interference on the decontamination effect of the photosensitizer's active photo-products. Suitable surfactants include some varieties of non-ionic surfactants and many varieties of anionic surfactants, including sulfates and sulfonates, and mixtures thereof, and mixtures thereof, for example alkyl sulfates and alkane sulfonates. Solid or liquid carrier particles may be added to aid in the application of and dispersion of photosensitizer. The selection of carrier particles depends upon the non-interference with the chemically reactive photoproducts. Suitable carrier particles include fine talc products, plastics, and alcohol aerosols. Various diluents can be added to adjust the viscosity or concentration of the photosensitizer, or to stabilize the photosensitizer. The selection of the diluent depends upon the environmental conditions and the delivery system. Suitable diluents include water and weaker acids.

Wetting and dispersion on the surface of an object can be aided by use of a surfactant. Selection of surfactant depends on the nature of the surface and the contaminant or biological agent. For aqueous aerosol solutions, a non-ionic surfactant, such as low carbon number alcohol ethoxylate or an anionic surfactant such as sulfates and sulfonates, including alkyl sulfates and alkane sulfonates, may be suitable. Free radicals from photochemical reactions will initiate oxidation and may set up chain reactions. Hydroperoxides will accumulate. In the presence of trace concentrations of catalysts, especially transition metal ions, or reducing and oxidizing agents, e.g., ferrous ions or bleach, the hydroperoxides will decompose. Increased temperature and exposure to UV light will promote the initial hydroperoxide formation. The oxidants so formed will react with the contaminants and pathogens, and so the surfactant can act as a photosensitizer as well as a wetting agent.

Photosensitizers include hydrogen peroxide, p-aminobenzoic acid (PABA) and its related compounds such as O-PABA, titanium dioxide (especially the anatase form), quinones and related compounds such as menadione (2-methyl-1,4-naphthoquinone), and the photodynamic sensitizers: 8-methoxypsoralen, acridine orange, methylene blue, eosin, and others.

In the case of hydrogen peroxide, it is known that intense UV light will yield two hydroxyl radicals with a quantum yield that is nearly unity. In addition, it is known that in the presence of certain metallic ions, (e.g., ferric iron and ferric oxide) and excess hydrogen peroxide, the photo-assisted Fenton's reaction, FE II with hydrogen peroxide to produce the hydroxyl, also leads to $Fe3+(aq)$ and perhydroxyl. The hydroxyl and perhydroxyl react strongly with most organic compounds.

Chemicals previously used as active ingredients in sunscreens, e.g., p-aminobenzoic acid (PABA), which can be absorbed into cells and upon absorption of a UV photon, produce thymine dimers. Related compounds such as O-PABA also can be absorbed into cells and produce other types of photon-induced DNA damage such as single strand breaks and breaks at guanine-cytosine pairs. Another compound previously used in sunscreens is titanium dioxide (especially the anatase form), a photoexcitable semiconductor. This compound acts as a photo-catalyst, i.e., it is not consumed in the photo-chemical reaction, but acts to enable the formation of an oxidant species. The anatase polymorph has strong UV absorption below 385 nm and low scattering below 300 nm. The absorption of a UV photon leads to the generation of conduction band electrons and valence band holes. These electrons and holes become trapped electrons and holes with the formation of surface hydroxyl radicals (and hydrogen ion). Because they are bound, the hydroxyls have little mobility. This is a disadvantage for treating surfaces unless the surface can be coated, i.e., painted with the anatase titanium dioxide as used by Dunn. However, other sensitizers, especially soluble liquids can be used in the presence of water, so that hydrogen peroxide is formed as a dimeric product that can diffuse a substantial distance, and with further UV absorption, become two hydroxyl radicals. Other compounds are known to be strong photosensitizers. Among these are the quinones and related compounds such as menadione (2-methyl-1,4-naphthoquinone), anthracene, rose Bengal, the anilides, and zinc oxide. These promote reactions that yield hydroxyl, hydroperoxides, and singlet oxygen species that have been shown to be effective in oxidizing organic contaminants. The photodynamic sensitizers include 8-methoxypsoralen, acridine orange, methylene blue, eosin, and others. In a preferred embodiment, the photosensitizer is of the photo-oxidative type and comprises a dilute aqueous solution of peroxy-containing compounds. An example is a weak solution of hydrogen peroxide in water, typically 0.5% to 1.0%, with an admixture of peracetic acid (PAA) in a concentration of 100–3000 parts per million by volume (ppmv) along with a surface active agent such as an anionic surfactant. One such solution is sold under the trade name ZEROTOL™ by BioSafe Systems, Inc., as a microbicidal drench, and includes some inert ingredients and other compounds to make the concentrate of the solution stable for storage. There are several commercial products that are suitable peroxy-containing solutions that may be used as photosensitizers. The use of hydrogen peroxide and PAA has the additional advantage that the post treatment by-products are water, acetic acid, carbon dioxide, oxygen and hydrogen. These make such a photosensitizer safe for use on a wide range of materials, including food, people, and animals, and without significant impact on the environment.

In general, the photosensitized reactions have rates that are strongly dependent on temperature. In addition, the formation of oxidative species is strongly dependent on the presence of oxygen (or air, or water). The diffusion of reaction products depends on the presence of a liquid film at the surface. Moreover, with diffusion in a solution, there is also scavenging by other species in the solution. The presence of readily oxidizable compound will deplete the concentration of radicals available for effecting the destruction of the contaminant of the disinfection. Examples of scavengers include alcohols and other organics, carbonates, nitrites, bromites, chlorites, and paramagnetic ions, etc. The presence of high concentrations of scavengers increases the required photon dose and photosensitizer dose. This is also the case for biological photo-protectorants such as glycerol. Thus, it may be necessary to know what quantity of these interfering compounds may be present on the surface to be treated.

Sufficient photosensitizer must be sprayed, delivered to the target surface, and adhered to the target surface so that upon illumination with UV light, enough photochemical reactions will occur to obtain a high degree of decontamination or disinfection. An estimate of the required amount of photosensitizer to be sprayed can be made from the following assumptions, which are given as examples for illustration:

1. target contaminant molecules or molecules of biological importance in the pathogen have a scale size dt in the range of 1–25 nm.
2. at least one photosensitizer molecule must be in the vicinity of the target molecule.
3. the photosensitizer molecule or its reactive (e.g., oxidative) photochemical reaction products can diffuse in the applied photosensitizer solution on the target surface, and have a typical diffusion distance, $\lambda \approx \sqrt{2Dt}$ where D is the diffusion constant and t is the time over which diffusion occurs,
4. the contamination or pathogens constitute clumps or a layer of material that can be taken to be an equivalent layer of uniform thickness.$\delta_t$ Assumption 1 implies a surface density of target molecules, $N_t \approx d_t^{-2}$ that is in the range of about $1.6 \times 10^{11}$ to about $1 \times 10^{14}/cm^2$ and a volume density of target molecules, $n_t \approx d_t^{-3}$ that is in the range $6 \times 10^{16}$ to $1 \times 10^{21}$. Assumption 2 implies that the density of photosensitizer molecules $n_s$ must be comparable to the density of target molecules, $n_s \approx n_t$. For exposure times that are on the order of a second or longer and contaminated or infected layers with thickness $\delta_t \geq 100$ $\mu$m, assumptions 3 and 4 suggest that $\lambda \geq \delta_t$, and ample transport of reactive species will occur within the layer. Based on these assumptions, it is found that for photosensitizer molecules of mass M, the fraction (concentration) of photosensitizer in a solvent of mass density $\rho$ (=1 g/cc for water), is $\xi \approx n_s M/\rho$. For hydrogen peroxide in water, these assumptions lead to an estimated concentration that is approximately in the range $\xi \approx 3 \times 10^{-4}$ to 10%.

An estimate of the volume of photosensitizer solution to be sprayed is made as follows. For a target of surface area A and affected layer thickness $\delta_t$, the volume at the target surface to be coated by the sensitizer solution is A $\delta_t$. A fraction $c_s$ of the photosensitizer solution aerosol will stick to the surface; this fraction is called the sticking coefficient. Of the aerosol sprayed, a fraction f will be incident on the affected surface. The fraction of the sprayed aerosol that comprises overspray is $(1-fc_s)$. The volume $V_s$ of sensitizer solution that must be sprayed to coat the area A is given by $V_s \approx \delta_t A f c_s$. Typical values may be in the range $\delta_t \leq 100$ $\mu$m, $f \approx 0.5$ (with lower values for low velocity, wide angle dispersion spray, and values approaching unity for electrostatically sprayed solution), and $c_s \approx 0.5$ (with a value approaching unity for electrostatically sprayed solution). Consequently, the volume of photosensitizer to be sprayed for a given area is estimated as $V_s/A \approx \delta_t f c_s \approx 25$ cm$^3$/m$^2$. Of course, these estimates are given only as representative values, and the actual value may vary over a wide range as the individual parameters may vary.

The surface 22 is then illuminated with a UV light unit 26. The UV light unit 22 may be a hand-held, pulsed UV lamp system, such as a 5 short-arc-bulb flashlamp array available from Clean Earth Technologies, LLC. The UV light unit 26 is placed in close proximity to the surface. Exposures of less than $10^5$ J/m$^2$ can effect several orders of magnitude deactivation of pathogens. Of course, control of the exposure and the photosensitizer concentration on the surface are needed to ensure consistent results of the process. If more than one square meter of surface is to be treated in a time period of a few minutes or less, then the output power of the UV source unit must be at least several hundred watts in the 200–300 nm part of the spectrum. Because the efficacy of the UV sources, in practice, is typically <25%, i.e., less than 25% of the input energy is delivered to the surface within the desired spectral range, the input power may be several kilowatts, and much of this power must be removed as heat from the source.

An estimate of the UV light exposure may also be made. If the yield of decomposed or altered molecules per incident UV photon is q, such that 0.1<q<1, typically, and the fraction of photons incident on a contaminated or infected layer that a pass through the layer to interact with a photosensitizer molecule is the transmission coefficient, T=1−A−R, where A is the attenuation coefficient, and R is the reflection coefficient, then, the fluence of incident UV photons $N_p$ (number of photons per unit area) necessary to react with $N_t$ target molecules per unit area is $N_p \approx N_t(qT)$.

The incident energy of UV photons that must illuminate a unit area is $\epsilon = N_p h_c/\lambda$., where, in this case, h is Planck's constant, c is the speed of light, and is the wavelength of the light. For light with $\lambda \approx 250$ nm, the photon energy is approximately 5 electronvolts (eV). If $N_t \approx 1 \times 10^{11} \rightarrow 1 \times 10^{14}$ cm$_2$, $T \approx 0.75$, and $q \approx 0.5$, then $\epsilon = 2 \times 10^{-7} \rightarrow 2 \times 10^{-4}$ J/cm$^2$ per monolayer of target contaminant molecules or target biological molecules. If a typical affected layer has a thickness $\epsilon_t \leq 100$ $\mu$m, then the thickness in equivalent monolayers is between about $4 \times 10^3$ and about $1 \times 10^5$. Consequently, the necessary incident UV light energy is estimated to be in the range 0.8 mJ/cm$^2$ to 20 J/cm$^2$. Typically, it is found that a fluence of about 5 mJ/cm$^2$ to about 100 mJ/cm$^2$ is sufficient to obtain a million-fold reduction, i.e., the post-treatment surviving fraction of organisms is $10^{-6}$ times the initial population, a 6-log reduction, in the bio-burden on a surface that has been sprayed with a peroxy-containing photosensitizer. The larger value applies to bacterial spores and sporulating bacteria. Lower fluences are sufficient to disinfect with vegetative bacteria and viruses.

The applied UV light intensity is preferably 1 to 1000 mW/cm$^2$, which is several times the fluence of UV light in sunlight. Pulsed light is more effective than continuous light. The rate of pulse is selected to achieve the desired fluence within the desired treatment time. The rate of pulse is also selected so that the decontaminating agents created by at least the immediately preceding pulse, are still present at the time of the next successive, pulse, so that the decontaminating agents and the photons from the next successive pulse cooperate in acting upon the decontaminants. This cooperative action has been found to be helpful in creating double strand breaks and irreparable breaks in pathogen DNA.

In contrast is the case without photosensitizer, wherein the photon must strike a vulnerable spot on a target molecule. In this case, the target scale size may be on the order of 0.2 nm. The corresponding number of targets per unit area is $N_t \approx 10^{16}$, which is 100 times greater than the sensitized case where mobility and chemical reactivity of the photosensitizer makes more efficient use of the light energy. As a result of the large value of $N_t$, the incident light energy per unit area must also be on the order of 100 times larger for the non-sensitized case, i.e., about 0.1 J/cm$^2$ to about 2000 J/cm$^2$.

Based on the above estimate for the photosensitized case, it is found that a UV light source emitting 1 kW of UV light with $\lambda$=330 nm, can treat more than approximately 10 m$^2$ per second, i.e., a treatment time that is on the order of 0.1 seconds per m$^2$ is necessary. Without sensitization, the treatment time is 1000 to 10,000 times longer. It is thus found that several features are desirable for an apparatus to apply the process in a practical manner. Energy efficiency is an important concern for a versatile, portable, and low cost apparatus. Because UV emitting sources, typically have efficiencies that are less than 50% in the spectral range of interest, waste heat management is a concern. It is also of interest to monitor the UV light incident on the affected surface, or equivalently, to monitor the light directed toward the surface, so that the necessary minimum exposure can be delivered without overexposure. Excessive exposure is energy wasteful and also may lead to deleterious effects to the surface. Energy efficiency is also a concern for the sprayer. If the spray is driven by an electrically powered compressor or fan, then sufficient work must be performed to propel the photosensitizer solution to the target surface. Electro-spraying improves the photosensitizer utilization and reduces overspray, but work must be performed to impart the electric charge to the aerosol. Moreover, heating of the photosensitizer may also be desirable to enhance the chemical reaction rates. This may especially be the case for treatment in cold environments. If the system is to be used for treating areas comprising many square meters, then quantities of photosensitizer solution on the order of liters must be provided. Therefore, significant energy may be needed to heat, charge, and propel the photosensitizer aerosol.

The sprayer 24 and the UV light unit 26 may be disposable, in which case it is not necessary for these devices to be sealed because after use they will be decontaminated or disinfected and discarded. Alternatively, the sprayer 24 and the WV light unit 26 may be sealed units so that they can be used in a contaminated or infected space and not become contaminated themselves. The sprayer unit 24 and the UV light unit 26 may also be consolidated into a single sealed unit. Consolidation of the sprayer unit 24 and the UV light 26 unit facilitates the cleaning of the units after use. The equipment can be decontaminated in accordance with methods of the present invention, or by conventional techniques, such as washing or immersion in a decontaminant or disinfectant.

The sprayer unit 24 and the UV light unit 26 can be operated remotely, or they can be manually operated, for example by personnel wearing protective garments and respirator apparatus as may be necessary. Furthermore, the personnel can be provided with protective eyeglasses, goggles, masks, and garments to avoid damage to their eyes or skin by prolonged exposure to UV light.

The process also provides for the decontamination or disinfection of a drifting cloud of hazardous chemical agent or infectious biological agent as might occur as a result of the situations cited above. In such circumstances, portable apparatus for applying the process is desirable. Also, means for remotely delivering the photosensitizer aerosol are desirable to ensure dispersion, mixing, and interaction with a drifting cloud containing contamination or infectious agents.

Figure 2:
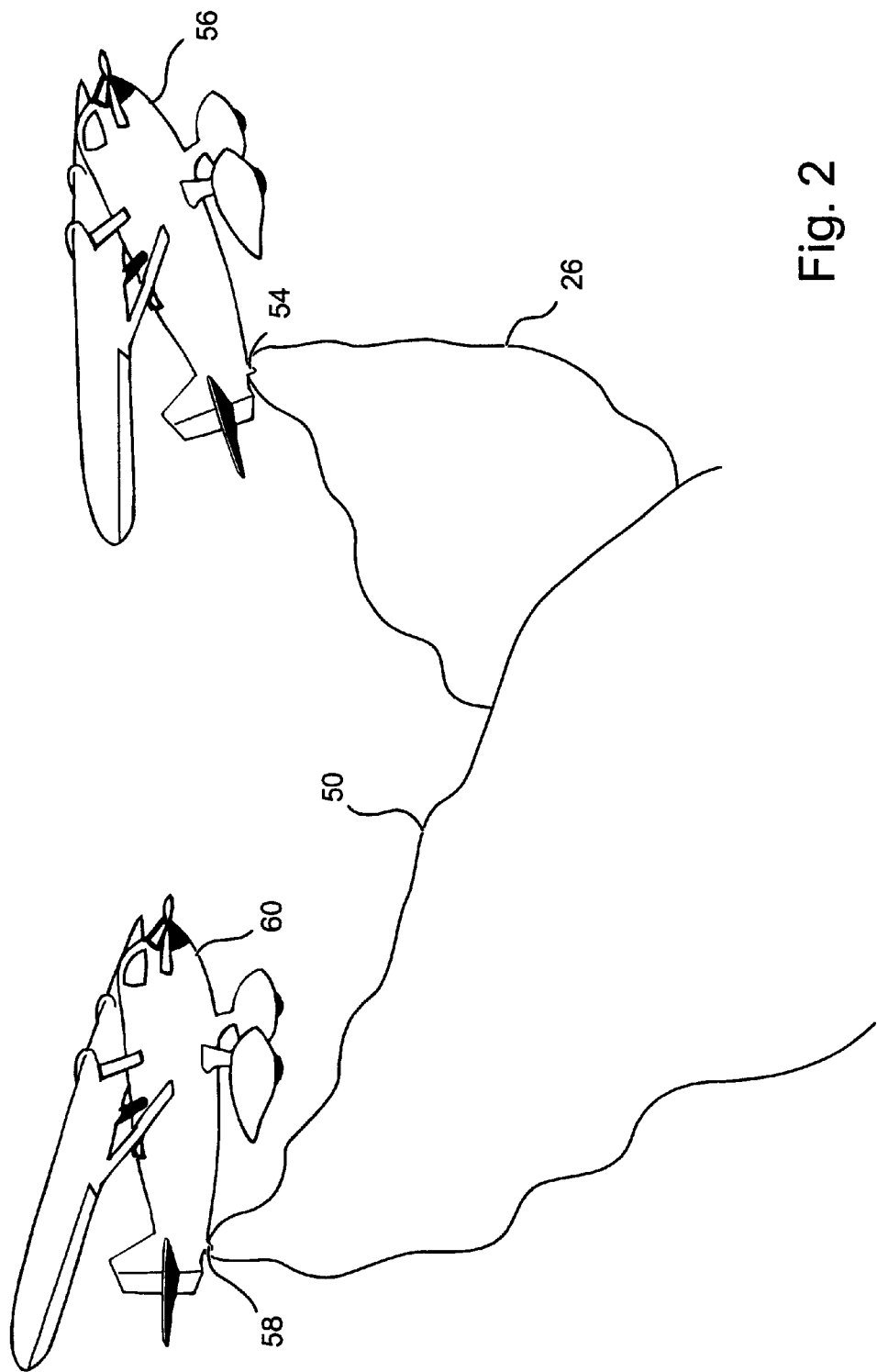
FIG. 2 is a schematic diagram of a process for decontamination of an aerosol cloud in accordance with the principles of this invention.

A process for decontaminating an aerosol cloud in accordance with the principles of this invention is illustrated schematically in FIG. 2. The cloud, indicated as 50 in the FIG. 2, may be drifting, or may be directed as a result of a sprayer, explosive munition, or other means. In accordance with this invention, a photosensitizer 52 is delivered to the cloud 50, for example with a sprayer unit 54 that is carried by an aircraft, such as a fixed wing airplane 56. The cloud 50 is then illuminated with UV light, such as with UV light unit 58, which can be carried by another aircraft, in this example, also a fixed wing airplane 60. Of course, other means of applying the photosensitizer 52 could be used, including, but not limited to, exploding artillery or rocket launched munitions, compressed gas foggers, aerosol cans, or mechanical means for dispersal and spraying. Such spraying means may be ground-based, on one or more projectiles, or on one or more airborne vehicles. The UV source unit 58, similarly, may be ground-based, on one or more projectiles, or on one or more airborne vehicles. The source may also be an expendable one, such as a pyrotechnic device.

To obtain the improved efficacy of electrostatic spraying of the photosensitizer, it may be necessary to employ any of several known techniques to avoid unwanted electrical charging of the platform from which the spraying is performed. These techniques include grounding the platform via a trailing wire, simultaneously spraying a second aerosol carrying charge of the opposite polarity from the platform, or providing means such as corona points to permit excess platform charge to leak off into the surrounding air. In the case of airborne platforms, a trailing ground wire might be deployed by a projectile that is launched from the platform.

Figure 3:
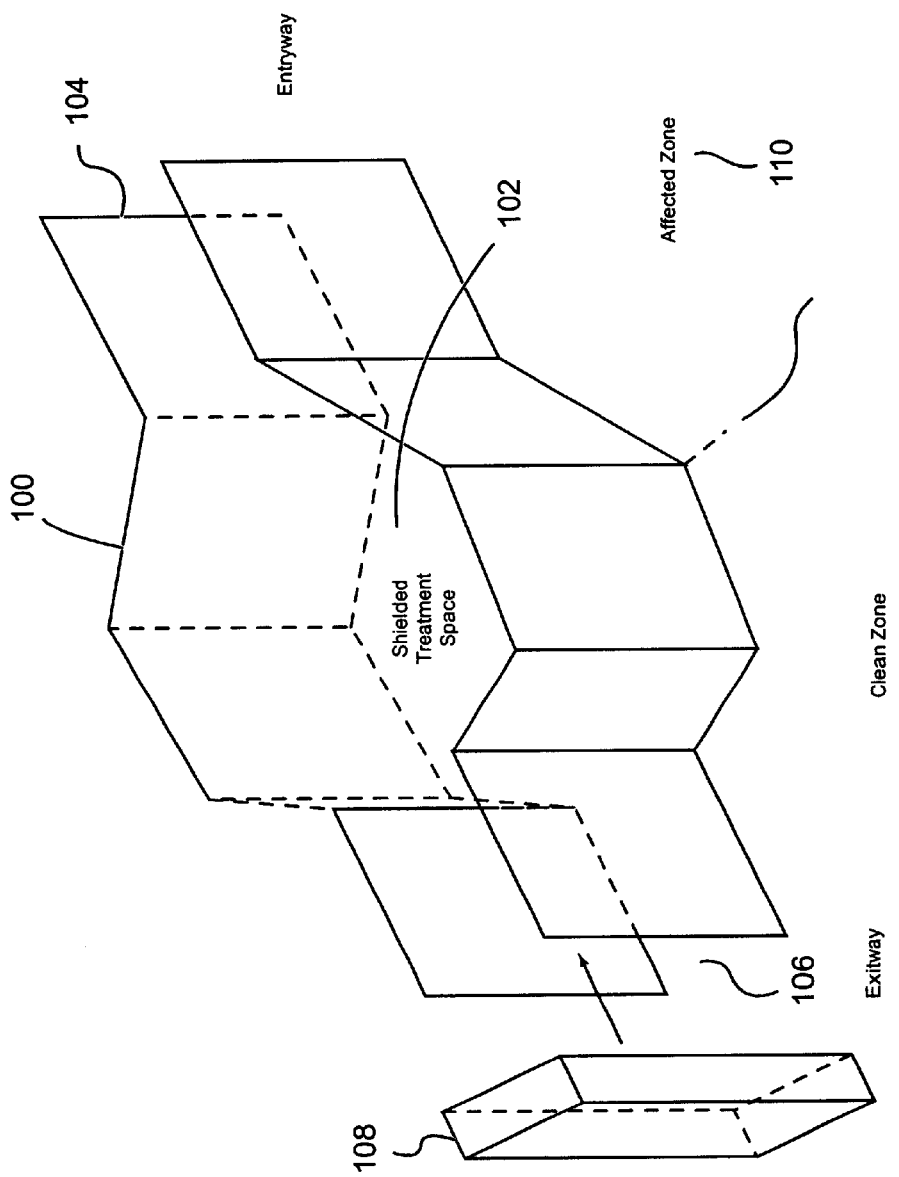
FIG. 3 is a perspective view of a barrier useful in carrying out decontamination processes in accordance with the principles of this invention.

One possible arrangement for carrying out the methods of the present invention is illustrated in FIG. 3, where the decontamination process is carried out within a portable barrier 100 that provides a shield against unwanted dispersal of the photosensitizer by wind, and also contains the effects of the process. Where the photosensitizer is applied by electro-spraying, the barrier 100 can be made electrically conducting to collect the excess aerosol photosensitizer, i.e., the overspray. The barrier 100 is preferably substantially opaque to ultraviolet light. Thus, the barrier 100 comprises a shield that defines a treatment space 102 within which the decontamination or disinfection process is performed, and protects the surrounding environment and the people and objects outside the treatment space. The barrier 100 surrounding the treatment space 102 can have access openings, e.g., entrance 104 and exit, 106, and a fan 108 that causes airflow into the exit 106 and out of the entrance 104, so that aerosol spray, and contaminants and/or pathogens are directed toward the entrance. In this way, the treatment space 102 can be situated on the perimeter of a contaminated or infected area, i.e., the affected zone, 110, and the process can be performed while ensuring that the area outside the affected zone is not contaminated or infected by objects or persons exiting from the treatment space.

Figure 4:
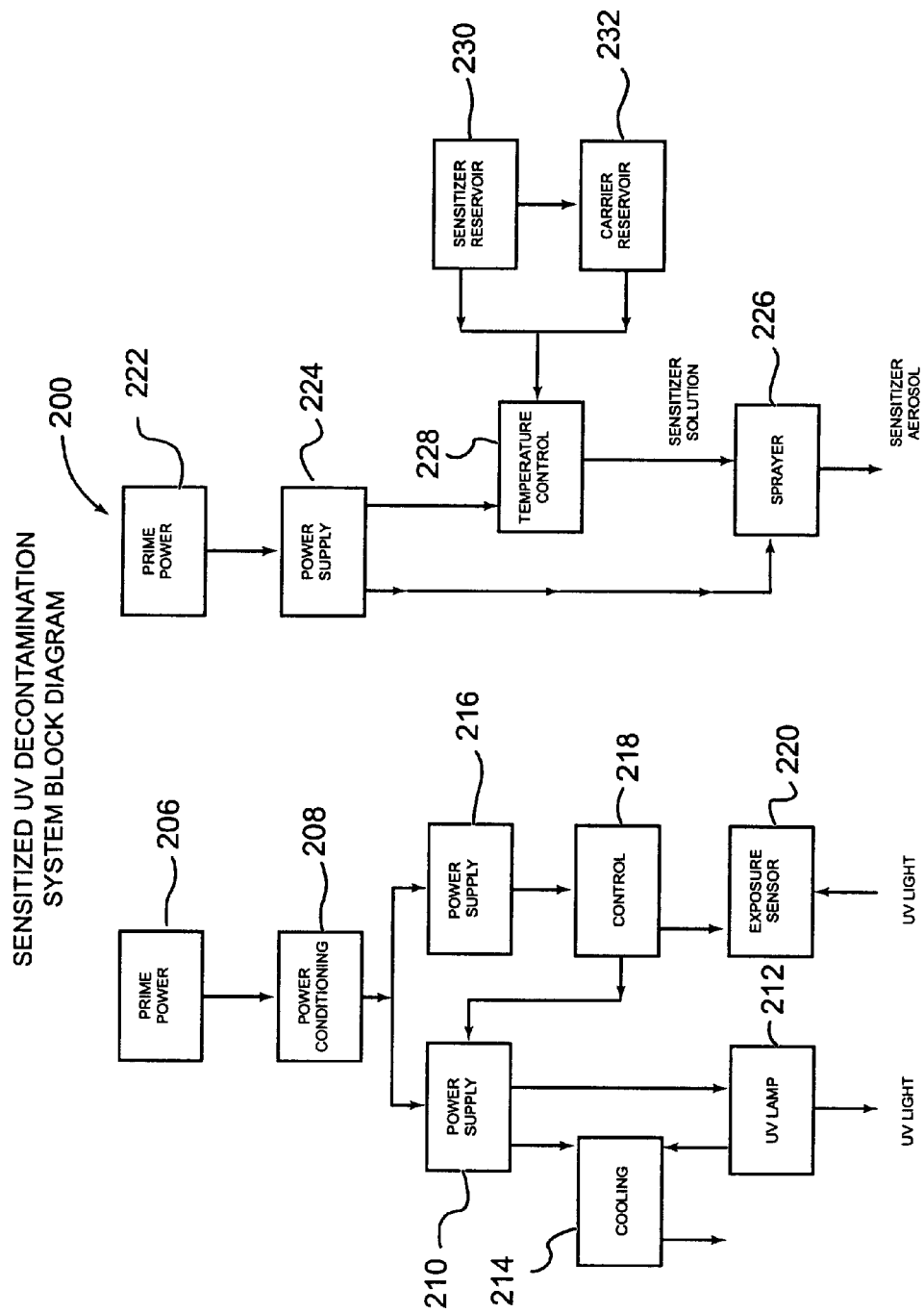
FIG. 4 is a block diagram of a first embodiment of an apparatus useful in carrying out decontamination processes in accordance with this invention.

An apparatus 200 for carrying out the methods of the present invention is shown schematically in FIG. 4. Apparatus 200 includes separate UV light source unit 202 and photosensitizer sprayer unit 204. The UV light source unit 202 has its own prime power source 206, which might be a bank of rechargeable batteries or a fuel cell, or a small portable generator. A power conditioner 208 can be provided to deliver power of appropriate voltage and current characteristics to power supply 210 that powers UV lamp 212 and UV lamp cooling system 214, and to power supply 216 that powers control 218. The control 218, preferably based at least in part on input from exposure sensor 220 controls the power supply 210 that powers UV lamp 212 and UV lamp cooling system 214. The exposure sensor 220 may be a photodetector coupled to an optical fiber that has a section of UV fluorescent material at its end, and optically connected to the UV lamp 212 by detachable fiber optic connectors. This arrangement permits the fluorescent material to be placed at a variable distance from the source. The photodetector output is amplified, typically, by a common operational amplifier circuit, and either displayed on a meter for the operator to read, or it may be input into an electronic circuit so that the lamp array output can be adjusted. The output of UV lamp 212 can be adjusted by changing the current provided to the lamp for continuous discharge lamps, and by changing pulse repetition frequency in pulsed lamps. In either case, the lamp output can be electronically adjusted using the sensor output.

The function of the exposure sensor 220 and control 218 subsystem is either to monitor the output from the UV lamp 212 or to monitor the incident light flux near the surface to be treated. When the desired exposure is attained, the control uses the exposure sensor signal as feedback to reduce the output of the lamp 212 or to signal the operator. In a preferred embodiment, the operator can reset an exposure indicator as the lamp 212 is directed toward a particular part of the target surface. When the desired exposure is reached, an indicator will signal the operator so that the light can be directed to another part of the surface. In another embodiment in which a pulsed lamp or lamp array is used, the control signal can be used to change the pulse repetition frequency to adjust the treatment rate as may be needed as the relative position or distance between the UV lamp 47 and the surface to be treated varies.

The photosensitizer sprayer unit 204 has its own prime power source 222, which might be an electric service, a generator, or a bank of rechargeable batteries or fuel cells. A power conditioner (not shown) could be provided to deliver voltage and current characteristics to power supply 224, which powers sprayer 226 and temperature control 228. The temperature control helps control the temperature of the photosensitizer, for example by controlling the temperature of the photosensitizer in reservoir 230 and/or the carrier in reservoir 232. The reservoirs may be heated or the photosensitizer solution may be heated just prior to its introduction to the sprayer subsystem. The sprayer unit must have pumps to pressurize or circulate the photosensitizer constituents and valves to adjust the flowrates of the various fluids and powders. These valves may be used to adjust the mixing ratios of the constituents of the photosensitizer solution.

Because the overall efficiency of UV source units is typically below 50%, a substantial amount of waste heat must be removed from the UV source unit 212. For a one kilowatt UV light output, the waste heat may amount to 1–5 kilowatts, and the prime power may amount to 2–6 kilowatts. Because in the preferred embodiment the UV source unit is compact and sealed, removal of waste heat power load is best done with a circulating cooling fluid. One possible cooling fluid is water, circulated in closed channels or tubes and attached for good thermal contact to the housing for the power supplies and lamp subsystems. For a permissible cooling fluid temperature rise of 40° C., a water flowrate of 0.36 to 1.8 liters per minute might be needed for a 1 kW UV output source. Heat may be removed from the cooling fluid by standard practices such as circulation by a pump through a radiator or other heat exchanger. An external fan or air turbine can provide airflow through the heat exchanger. In the case where a shield is situated around the treatment area to define the treatment space, the airflow from the fan may be used to control and direct the airflow in the treatment space.

In a preferred embodiment featuring an advanced spraying system, the aerosol suspension of the UV photosensitizer is enhanced by using a spraying unit with a high-pressure pump, a temperature-controlled reservoir, a flow-metering system, and a precision diamond drilled micron diameter nozzle as an applicator. The sprayer is tailored to deliver a desired distribution of aerosol droplet diameters, to improve the ability of the photosensitizer aerosol to rapidly cover surfaces and scavenge drifting aerosol agents, bacteria and chemical compounds.

Figure 5:
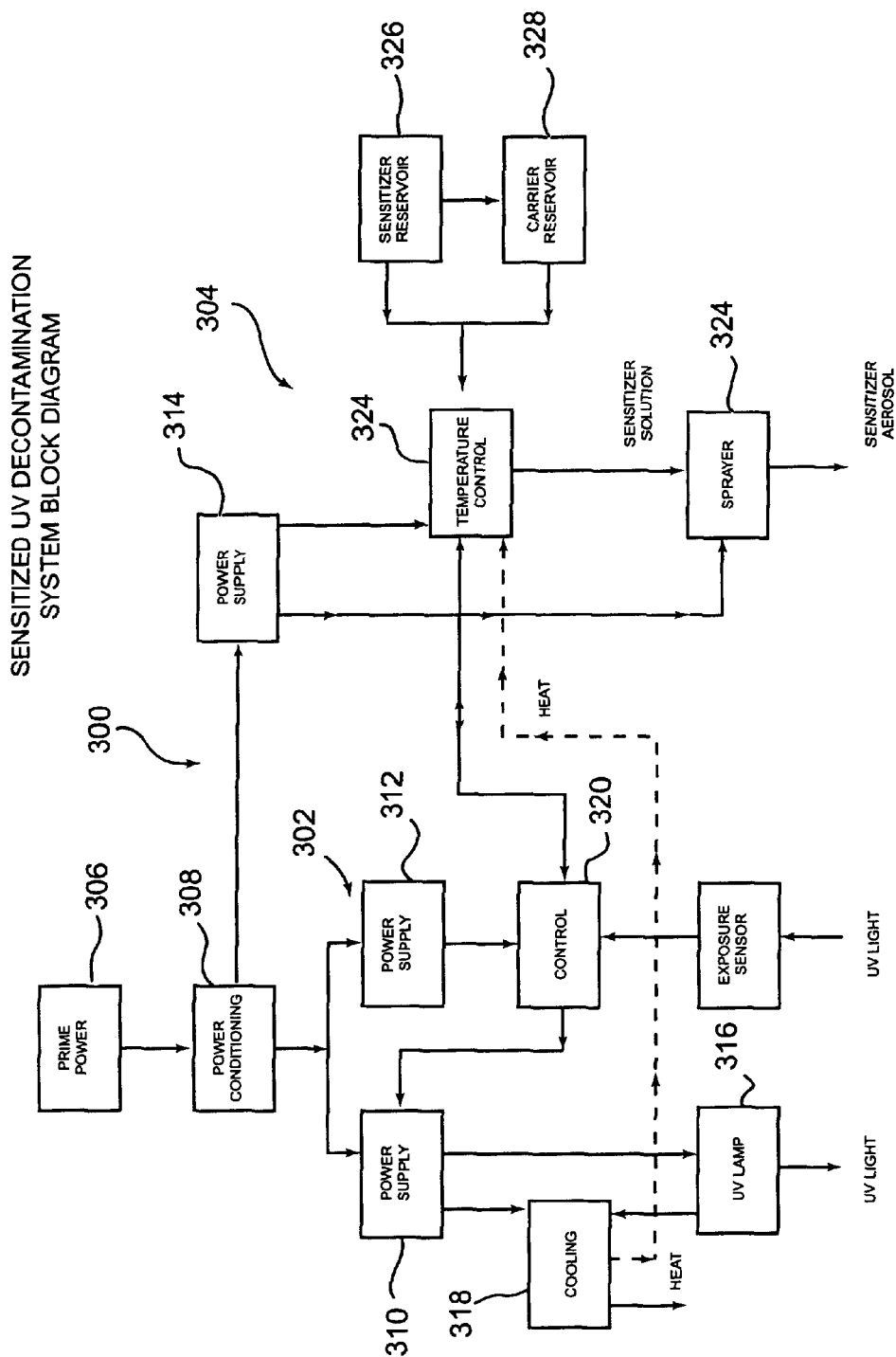
FIG. 5 is a block diagram of a second embodiment of an apparatus useful in carrying out decontamination processes in accordance with this invention.

Another embodiment of an apparatus for implementing the methods of this invention is indicated generally as 300 in FIG. 5. In apparatus 330, a UV source unit 302 and the photosensitizer sprayer unit 304 are integrated powered by a prime common power source 306. A power conditioner 308 distributes the power with the appropriate voltages and currents to power supplies 310 and 312 of the UV source unit 302 and 314 of the sprayer unit 304. The power supply 310 powers UV lamp 316 and UV lamp cooling system 318; power supply 312 powers control 320. The control 320, preferably based at least in part on input from exposure sensor 322, controls the power supply 310 that powers UV lamp 316 and UV lamp cooling system 318. Power supply 314 powers sprayer 322 and temperature control 324. The temperature control 324 helps control the temperature of the photosensitizer in reservoir 326 and/or the carrier in reservoir 328. An advantage of integrating the UV source 302 and the photosensitizer sprayer 304 is that excess heat from the UV lamp 316 can be used to heat the photosensitizer. The heat transfer between the heat exchanger of the cooling system 318 may be connected to temperature control 324 for circulating fluid. This fluid removes heat from the heat exchanger of the lamp cooling system 318, in addition to a secondary cooling flow of air or other fluid. The relative amount of heat removed by the heat transfer fluid and the secondary cooling can be adjusted by the temperature control system 324 by the opening and closing of valves or airflow baffles and dampers. Adjusting the heat transfer to the photosensitizer is then accomplished by adjusting the flow rate at the exhaust heat cooling fluids at the lamp cooling subsystem.

Figure 6B:
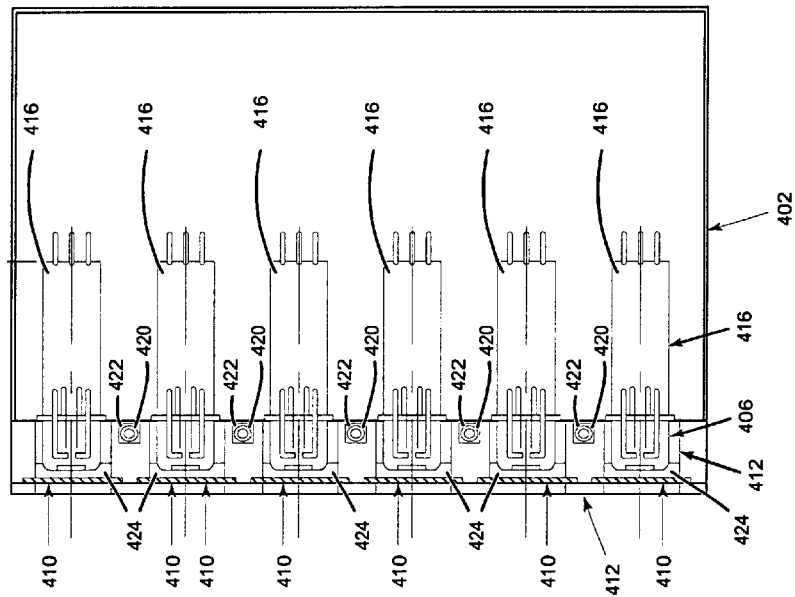
FIG. 6B is a vertical cross sectional view taken along the line 6B—6B in FIG. 6A.
Figure 6A:
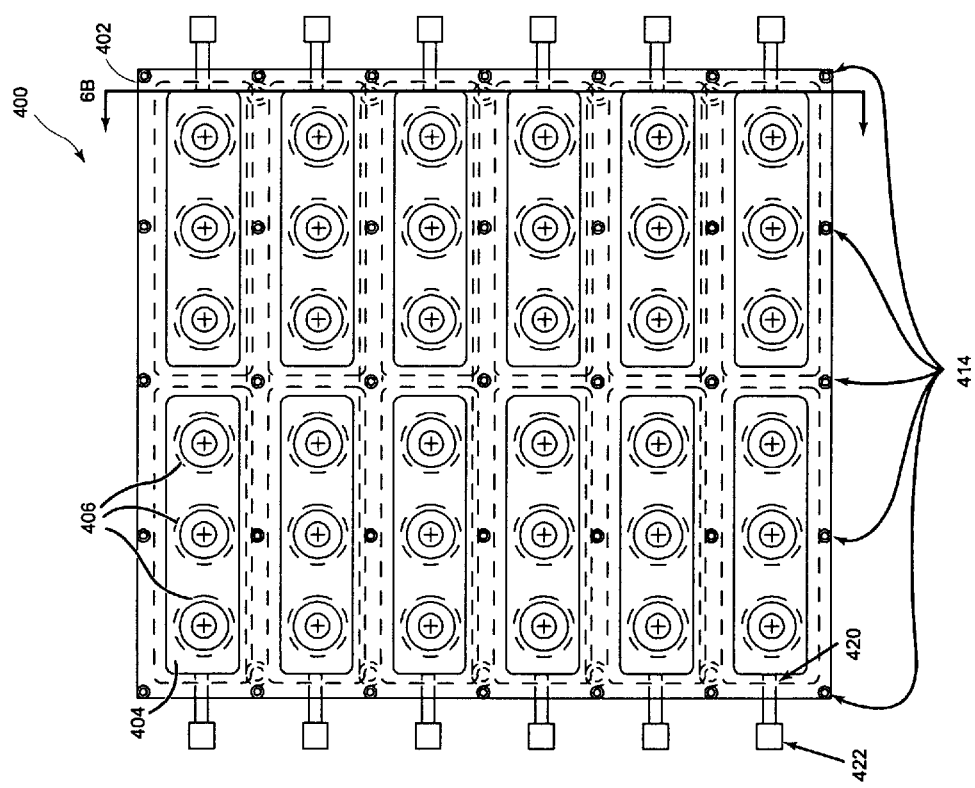
FIG. 6A is a front elevation view of a UV light emitting source comprising a multi-lamp array of flashlamp bulbs.

One possible UV light source adapted for use with this invention is indicated generally as 400 in FIGS. 6, 6A and 6B. UV light source 400 comprises a housing 402 containing an array 404 of flash lamp bulbs 406. The housing 402 can be made of plastic, metal, glass, or other material that provides an impermeable barrier to the contaminants or pathogens. In the preferred embodiment, the housing 402 forms the top, bottom, left, right and back sides of a rectangular prismatic box. The sides may be removable panels that are held by removable fasteners and sealed by any of several conventional techniques such as adhesive sealant, o-rings or gaskets, or may be fused, brazed, or welded construction. The front of the housing is a window assembly 406 that comprises a frame 408 in which are mounted windows 410 that are substantially transparent to the UV light. These windows are held in place by any of the sealing techniques listed above and also held mechanically by a rigid grid 412 that is held to the main portion of the window assembly 406 by fasteners 414, e.g., metal machine screws. A preferred sealing technique is by gluing the windows 410 in place with silicone rubber adhesive, and with a thin bead of sealant that is less than 1 mm thick. The silicone rubber provides a cushion to protect the window against mechanical shock but is sufficiently flexible to accommodate differential thermal expansion of the windows. Any high temperature resistant elastomer (e.g., silicone, fluorocarbon, etc) may be used that is also resistant to the chemical contamination with which the system is used. Silicone room temperature vulcanizing (RTV) sealant may be used at operating temperatures as high as 240° C.

The windows 410 are preferably made of fused quartz having low water and hydroxyl (OH) content. Such material is resistant to crystobalite formation of water containing quartz. It also can have a UV light transmittance of 90% or greater in the spectral range 200–325 nm. An antireflection coating may also be applied to the window surfaces to enhance the source unit output. Another useful window material is sapphire, but this has a lower transmission coefficient of about 70%.

UV light is generated by short pulse, high current density, high temperature electric arcs having a length of a few mm and being contained within flashbulbs 406. The pulsed high-pressure lamps are often xenon flash lamps, which are attractive because a significant fraction of their total light output is in the UV part of the spectrum. This is especially the case for short arc, pulsed xenon lamps that have relatively low output in the red and infrared part of the spectrum and may emit as much as 40% of their total output in the UV range with wavelength less than 300 nm.

In a preferred embodiment, the flashbulbs 406 are high pressure, short-arc xenon discharge bulbs, but other discharge gases may be used. Commercial examples of such bulbs typically have an integral reflector that is inside the bulb and a quartz or sapphire window that is highly transmissive of UV light. Examples include mercury vapor, mercury vapor with Penning or buffer/diluent mixtures, excimer gases, and other inert gases. These short-arc bulbs offer low spectral content at long wavelengths such as those above 400 nm in comparison with linear discharge lamps. A trigger transformer, socket, and related circuit components are housed in a pulser assembly 416 for each lamp. The flashbulbs are powered by capacitor discharge. The capacitors may be switched by initiation of the arc in the flashbulbs 406, which is triggered by a high voltage trigger pulse. The trigger pulse is generated by SCR (silicon controlled rectifier) or IGBT (isolated gate bipolar transistor) switching of a trigger capacitor through the pulse transformer of pulser assembly 416, or other pulsed voltage source. Charging of the main discharge capacitor can be efficiently done by resonant charging with a high frequency, chopped electrical current and an IGBT series switch that delays the commencement of recharging after the previous discharge. This delay in recharging allows the discharge in the bulb 406 to de-ionize sufficiently so that the discharge is effectively extinguished prior to recharging. This prevents the discharge from 'holding-on' and preventing efficient recharging and damage to the bulb. Good heat transfer from the flashbulbs 406 to the window assembly 406 is provided by heat sink clamps 418. A high thermal conductivity paste may be used in the joint between the flashbulb and the heat sink clamp and between the window assembly and the heat sink clamp to aid in thermal transfer. Heat transfer from the window assembly 406 to the cooling fluid in cooling tube 420 is accomplished by a brazed, soldered, or compression gasket 422. Additional cooling of the flashbulbs 406 and windows 410 may be necessary at very high average power. This additional cooling can be provided by circulating cooling gas in the space 424 between the windows and the flashbulbs 406. The cooling gas is fed into the space 424 via tubes that connect to compression fittings 422 and through channels or holes in the window assembly 412. The cooling gas is preferably helium because of its large heat capacity, inert nature, and thermal conductivity, but could also be dry air, nitrogen, an inert gas, or other non-reactive gas.

Figure 7A:
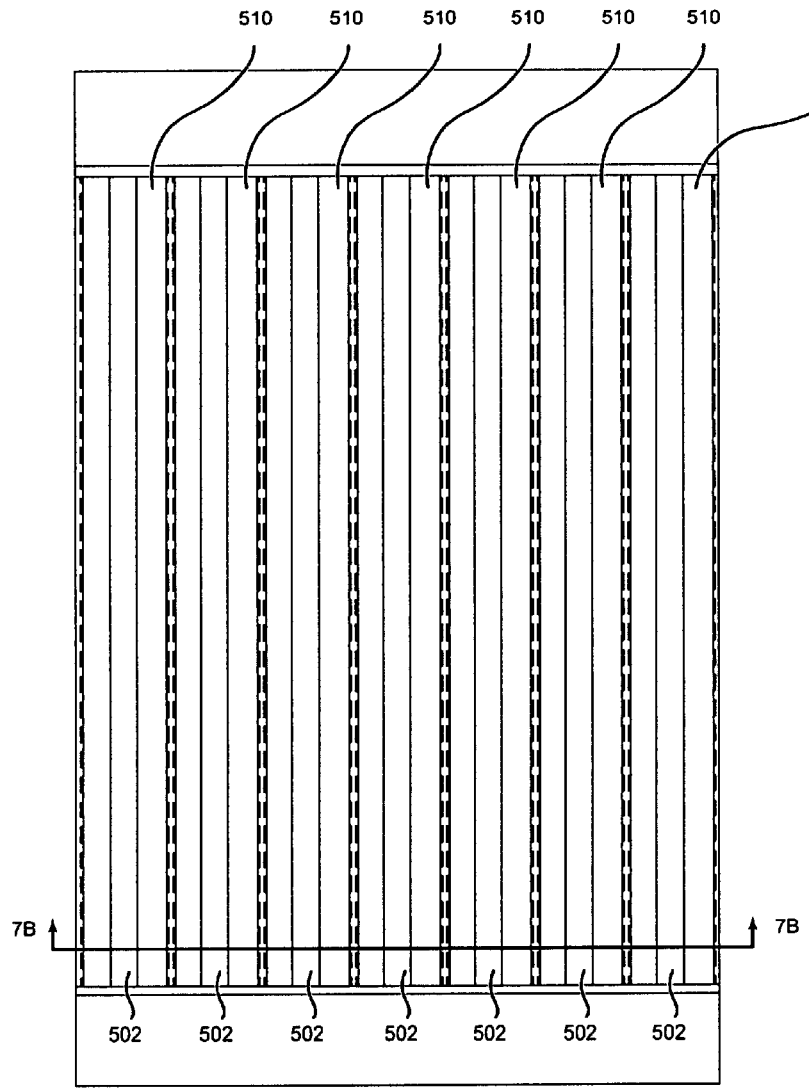
FIG. 7A is a drawing of a UV light emitting source comprising a multi-lamp array of linear lamps.
Figure 7B:
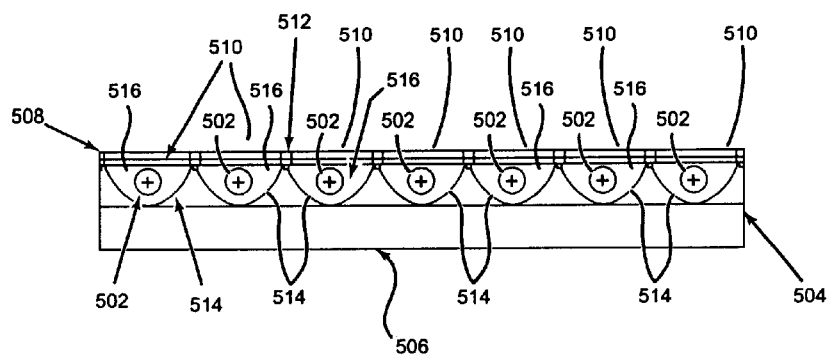
FIG. 7B is a vertical cross sectional view taken along the line 7B—7B in FIG. 7A.

Another possible UV light source adapted for use is indicated generally as 500 in FIGS. 7A and 7B. The UV light source 500 comprises one or more linear discharge lamps 502. These lamps 502 may be continuous discharge lamps or pulsed flash lamps. As shown in FIGS. 7A and 7B, the UV light emitting source comprises a multi-lamp array of linear discharge lamps 502. In this arrangement, the UV source unit is surrounded by a sealed housing 504 that has construction of the types described above. The housing provides a space 506 for power supply, pulser, cooling, control, and sensor components. A window assembly 508 positions windows 510 of the types described above and sealed with the above-mentioned techniques, and additionally held fixed in place by a clamping grid 512. The output of the UV source unit is improved by using parabolic reflectors 514 with the discharge lamps 502 placed at the foci of the parabolas. These reflectors may be of any material as long as the surface adjacent to the lamps is highly UV reflective. Such a reflective surface may comprise a vapor deposited or very highly polished aluminum coating, a multi-layer dielectric interference coating. The coating is preferably a vapor deposited aluminum coating on a smooth aluminum substrate, with the aluminum coated also covered by an adhering fused quartz coating or a dielectric coating that protects the reflective nature of the aluminum. Cooling channels or tubes fixed to the housing, reflector, window assembly, and lamp components help cool the housing and the reflectors. Flowing gas as a heat transfer fluid in the spaces 168 between the reflectors and the lamps can provide additional cooling.

Figure 8:
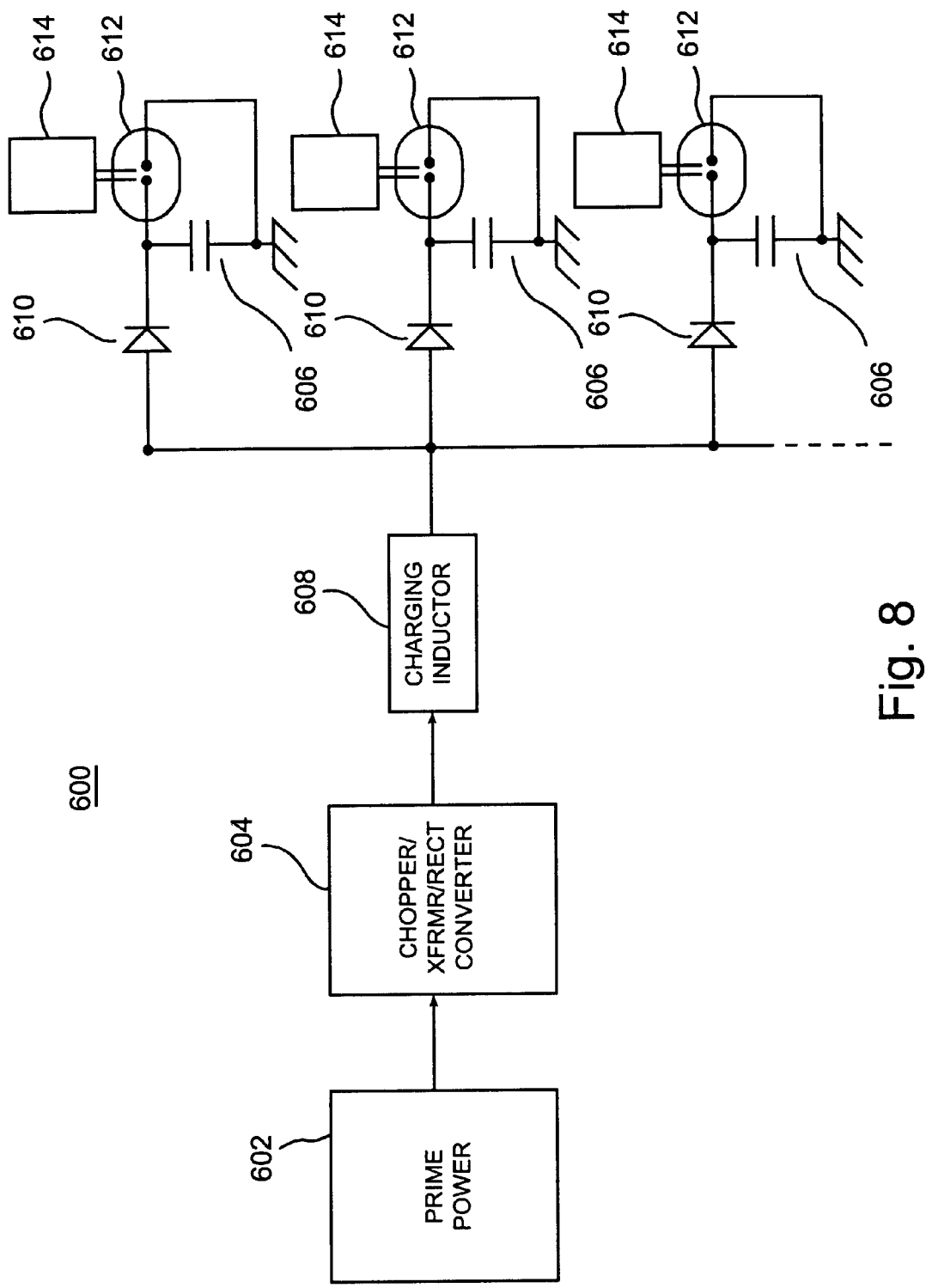
FIG. 8 is a schematic diagram of a circuit for powering pulsed UV emitting flashlamps.

A circuit 600 for powering pulsed UV emitting flash lamps is shown schematically in FIG. 8. The prime power source 602 is connected to a power conditioner 604 to connect the power to a high voltage (typically 0.5–5 kV, direct current. The high voltage resonantly charges the discharge capacitors 606 (total parallel capacitance C) through inductors 608 (series inductance L) and blocking diodes 610. The charging time is the quarter-wave rise time of the LC circuit. The diodes prevent the discharge of the capacitors during the interval following full charging of the capacitors and the triggering time of the discharge through the flash lamps 612. The discharge is initiated by high voltage trigger pulses to each pulse by pulser 614. This circuit arrangement is superior to charging the capacitors through resistors because the energy dissipation in the resistors is avoided. Also, inverter/converter high voltage power conditioning can be performed with high frequency switches and high chopping frequencies so that the step-up transformer by which the high voltage is generated can have a smaller ferromagnetic core and be made small. For versatility and portability, it is desirable that the UV light source be compact and light weight.

The photosensitizer solution and the sprayer unit that generates and directs the aerosol spray are critical elements of the process. Sensitizers are ch photons or undergo reactions in the presence of UV light and produce chemical changes or reaction products that produce changes in the contamination or in the pathogens. These photochemical reactions with the sensitizer may also be accompanied by the direct action of the UV photons.

The photosensitizer may be delivered as an aerosol comprising an aqueous or non-aqueous solution, carrier powders or particulate, or as condensate from a sprayed vapor or an aerosol fog. In the case of target surfaces on objects, the photosensitizer aerosol strikes the contaminated surface and coats the surface and the chemical/biological agents thereon. Electrostatic charging of the spray as the aerosol is launched, i.e., electro-spraying helps ensure that the aerosol adheres to the surface and to the chemical/biological agents. In the case of an aerosol cloud of chemical/biological agent, electro-spraying acts to enhance scavenging of drifting aerosols containing chemical, biological agents, bacteria, or chemical compounds.

Figure 9:
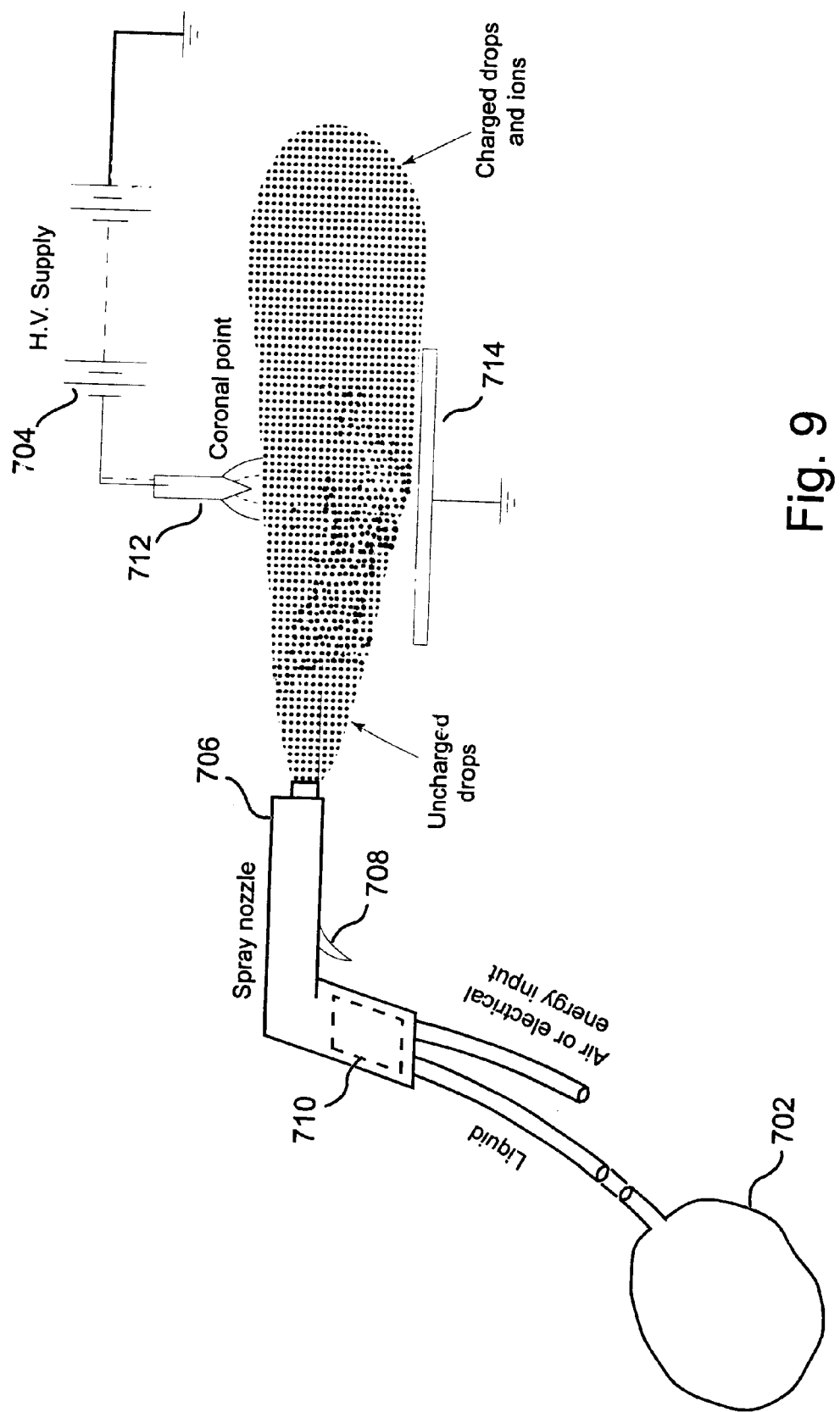
FIG. 9 is a schematic diagram of an electrostatic-aerosol sprayer for directing the photosensitizer onto a surface of an object or into a cloud.

An electrostatic-aerosol sprayer for directing the photosensitizer onto a surface of an object or into an aerosol cloud, indicated generally as 700, is shown schematically in FIG. 9. The system consists of a reservoir 702 which is electrically isolated from ground potential, a high voltage power supply 704 capable of operating in the range 20–100 kV, a nozzle 706 which can be biased at high voltage, a valve controlled by trigger 708 which allows the flow to be controlled, a pump or aerosol delivery system, a metering system 710 and corona discharge electrodes 712 and 714. As the photosensitizer mixture of carrier solvent and UV sensitizer flows through the high voltage biased nozzle 706, the liquid is aerosolized and charged. Charging at the nozzle might also occur because of the triboelectric effect. In a preferred embodiment, the droplets become charged, as the sensitizer is aerosolized, by the corona discharge between the pointed electrode 712 and ground potential electrode 714, and powered by the high voltage power supply.

The electrostatic charge is applied either prior to aerosolization of the photosensitizer solution or powder, or after the aerosol has been launched toward the target. The distribution of the particle droplets is tailored to adhere to the surface to be treated or to scavenge nearby air-borne particles by adjusting the high voltage applied to the nozzle, the flow rate, and the polarity of the power supply. As shown in FIG. 10, embedded charge 750 electrostatically attracts nearby aerosols 752 with embedded charge, allowing diffusion of the sensitizer into the target droplet 754, or surface as shown schematically in FIG. 10. Electrostatic application of the sensitizer to the target surface also enhances the coverage of the surface and allows the applied droplets and particles to more strongly adhere to the surface.

Photosensitized UV decontamination and disinfection is at least in part the result of UV photons interacting with the photosensitizer and target materials to produce reactive species, principally oxidative radicals, that chemically react with the contaminant or, in the case of disinfection, with chemicals that are important for cell reproduction, metabolism, or integrity. The type of photosensitizing reactions can be categorized as follows:

1. Photo-oxidative: photosensitizers produce hydroxyl radicals OH, peroxides OOH, hydroperoxides, or singlet oxygen O(1D), as well as many other reactive species such as O2-(the super-oxide), alkoxyls, and related species;
2. Photo-cyto-toxic: photosensitizers produce pyrimidine dimers that interfere with DNA repair and replication, multiple fragmentation of DNA strands, or they produce enzymatic changes that interfere with cell function or replication;
3. Photo-dynamic: enhanced absorption of UV by 'dyes' leads to multiple fragmentation of DNA strands.

Delivery of the photosensitizer can be made by several methods. The use of an electrically-powered pumped sprayer or an electro-sprayer has been described above. An aerosol spray of a simple sensitizer solution such as an aqueous solution of hydrogen peroxide ($H_2O_2$) and PAA also can be produced by a manually pumped sprayer, by pressurized aerosol spray can using a propellant gas, or by a compressed gas. Additionally, there are other means to deliver and disperse an aerosol spray of photosensitizer solution in situations that are not amenable to hand held or fixed installation devices. These situations include the inside of ducts and low accessibility confined spaces, wide area clouds and surfaces, and aerial aerosol clouds. For these situations, a fogger or canister burst delivery of the aerosol photosensitizer spray are well suited. The various means for spraying the photosensitizer aerosol provide the capability of obtaining flow rates for the spray system that can span the range from a few tenths of a liter per second to thousands of liters per second, depending on the application.

Figure 11:
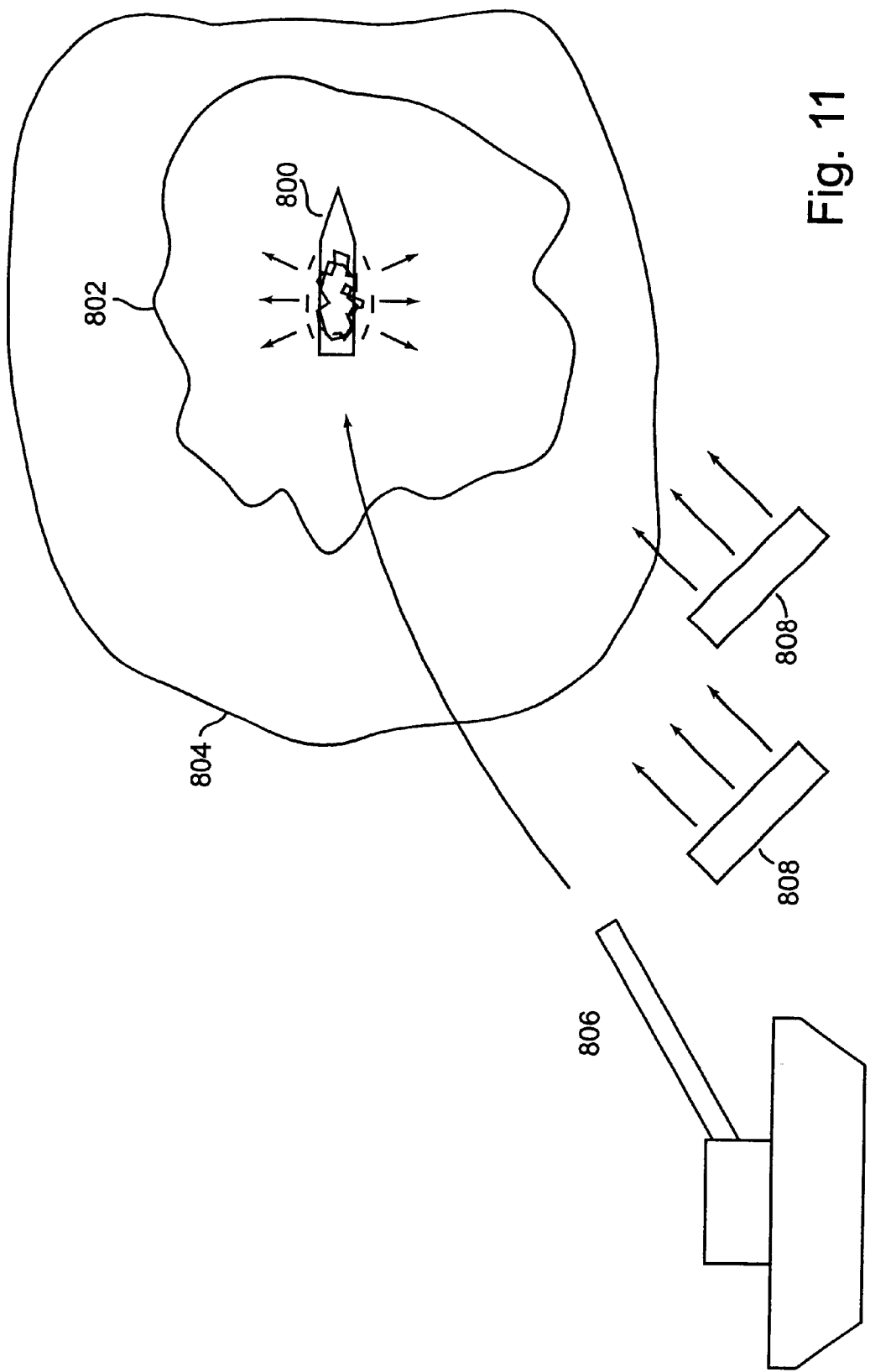
FIG. 11 is a schematic diagram of the arrangement for spraying the photosensitizer by means of an exploding canister, in accordance with one aspect of this invention.

An arrangement for spraying the photosensitizer by means of an exploding canister (i.e., an advanced canister-burst applicator) is shown schematically in FIG. 11. This type of dissemination is well suited for dispersing an aerosol over a wide area. The canister 800 comprises a reservoir or plenum that is filled with a sensitizer and carrier solvent, and an internal charge of explosive. The internal explosive charge is exploded using a timed fuse, or radio controlled detonator. The explosion ruptures the reservoir and the photosensitizer 802 is aerosolized and mixes with a drifting aerosol cloud 804. The photosensitizer precipitates onto the surface of drifting aerosol droplets and particles and combines therewith. The canister is delivered to the spatial region of interest via a shell fired by an artillery piece 806, or by rocket, aerial drop, or by other launching means that may use explosives, compressed gas, electromagnetics, or other advanced kinetic energy technologies. A bank of UV source units 808 can be directed to illuminate the photosensitized cloud, or the UV sources can be carried by an aerial vehicle. For perimeter defense, the UV light units can be arrayed near the perimeter of the area to be protected, and the canister applicators can be used to ensure that the sensitizer aerosol is dispersed and mixed with the contaminated or infected cloud prior to arrival in the vicinity of the perimeter. The illumination can be performed as the cloud approaches so that the photons can be efficiently used.

Figure 12:
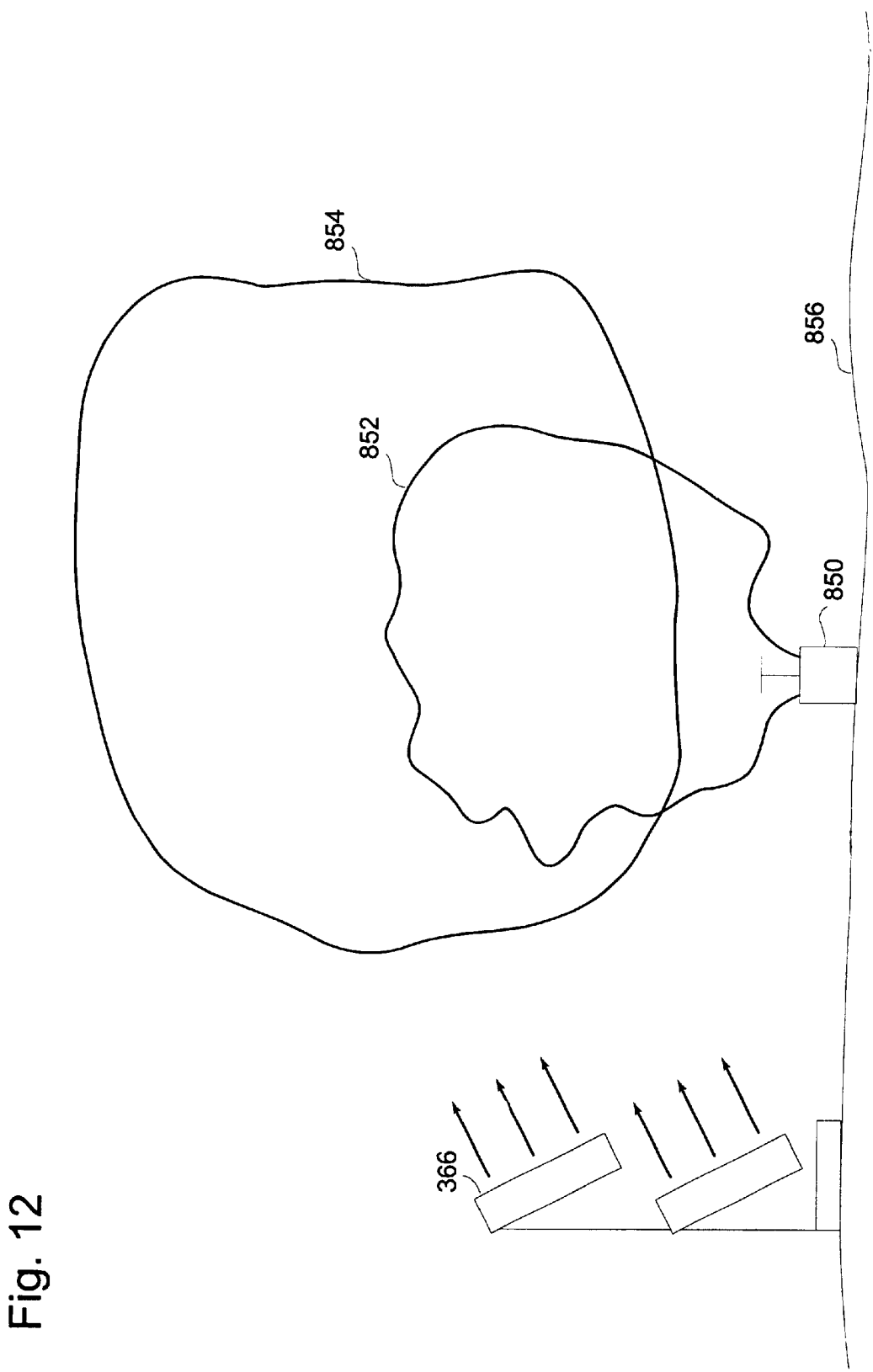
FIG. 12 is a schematic diagram of the arrangement for spraying the photosensitizer by means of a compressed 'area fogger;'

FIG. 12 is a schematic diagram of the arrangement for spraying the photosensitizer by means of a compressed "area fogger". In this arrangement, the fogger 850 sprays the photosensitizer solution 852 into a contaminated or infected aerosol cloud 854 or onto a surrounding affected area 856. As with canister spraying, the UV source unit(s) can be arrayed and situated in the vicinity of the perimeter of the area to be protected. A fogger is also suited for delivery of the photosensitizer to wide areas and to surfaces such as skin, fabric, and the interior of building ventilation ducts. The sprayer can be a simple atomizer, which atomizes the UV photosensitizer along with its carrier solvent into droplets. If the droplets are tailored to remain in aerosol form, the typical diameters should be in the range of 1–50 μm diameter. The aerosol droplet size for rapid precipitation onto a surface would preferably be larger than 50 μm in diameter.

For many photosensitizers, a sufficiently high intensity of UV light in the correct part of the spectrum, i.e., light having the proper wavelength, is required to obtain the desired reaction products and yields. For example, with pulsed UV light having a wavelength in the range of 200–300 nm, hydrogen peroxide is dissociated efficiently and rapidly into 2 hydroxyl radicals. Light of longer wavelength or lower intensity results in substantially reduced yield. In the case of reactions involving UV and ozone to produce single oxygen, UV light with wavelength below 300 nm is also desirable. Use of light with longer wavelengths has lower yield of singlet oxygen and a greatly increased yield of triplet oxygen that is much less reactive than the singlet species. It has also been shown that prior illumination of DNA in cells with UV light having wavelengths longer than 300 nm tends to inhibit the repair mechanisms and make the cell and its DNA more vulnerable to short wavelength UV light damage. Therefore, in the case of disinfection, it is desirable to have a light source that emits some light at wavelengths longer than 300 nm in addition to its predominant emission at wavelengths in the 200–300 nm range. It is also desirable to repetitively pulse illuminate the surface so that the benefits of prior illumination by the longer wavelength components can be exploited as well as to allow time for diffusion of the peroxides and their dissociation products in the solvent layer on the surface. With sufficient liquid on the surface and sufficient wetting, some of the solution and the reactive products can seep into cracks and crevices to obtain decontamination or disinfection in locations where the UV light cannot shine or penetrate.

In practice, the time required for disinfection is proportional to the amount of bacteria, or colony forming units present per square meter of material and total mass of the material present (CFU/ml). The disinfection time is also a function of the photosensitizer concentration, the aerosol particle density, the specific wavelength of UV light applied, and the fluence level of light. The energy per kilogram of contaminated material is proportional to the exposure, i.e., the product of the power of the UV source and the illumination time, and it is inversely proportional to the molecular weight of the material, the volume, the initial concentration and the final desired concentration. The energy per kilogram of material will also depend strongly on the diffusion time through the bacterial cell wall, and the quantum yield of radicals, or dimer reactions and the coupling efficiency of the light to the photosensitizer.

Figure 13:
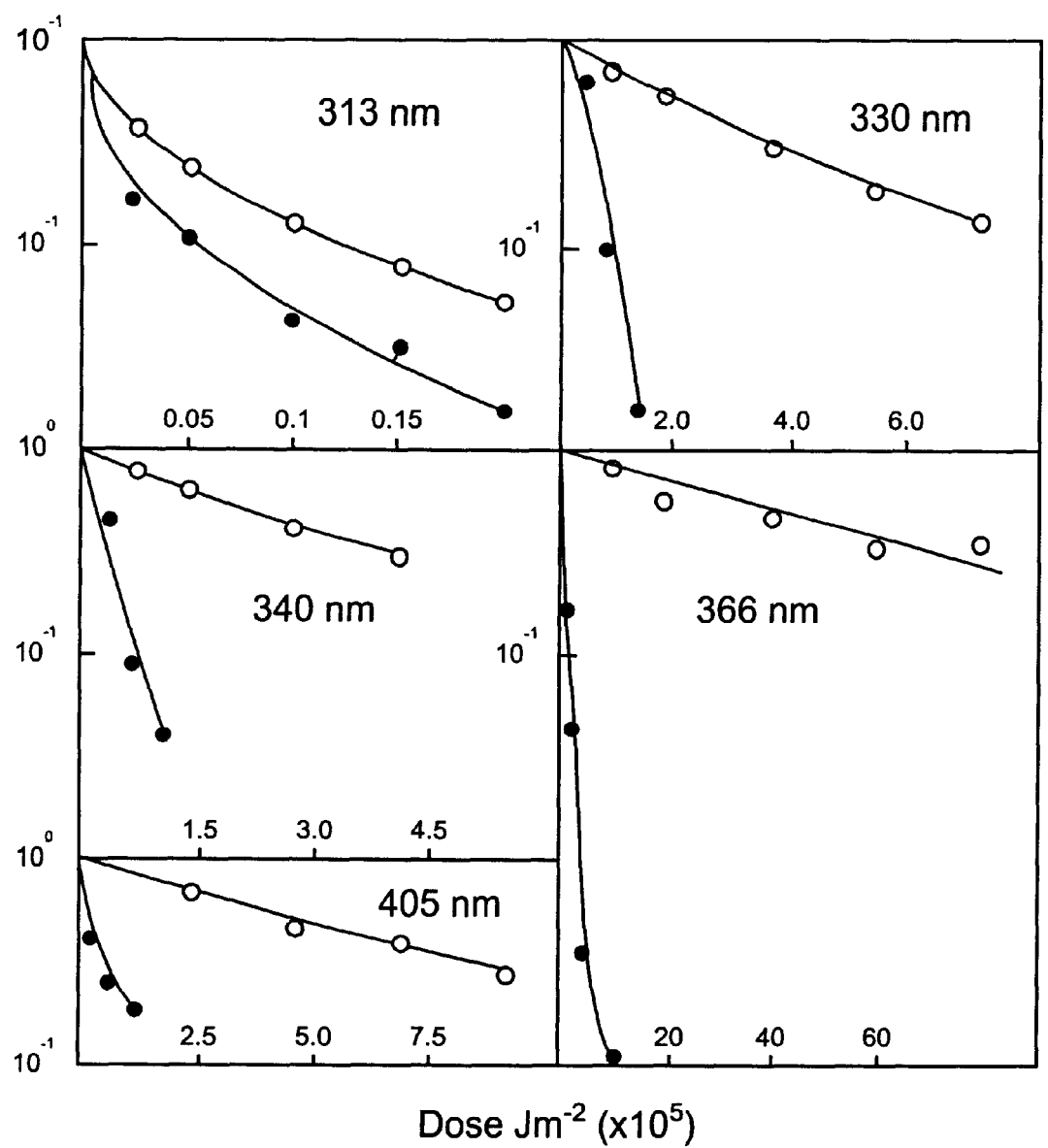
FIG. 13 is a group of graphs of data for the deactivation of a bacterium JC5088(recA) by ultraviolet light in the presence and absence of hydrogen peroxide photosensitizer; shown is the surviving fraction of spores as a function of UV light dose for four different wavelengths of the light.

Use of an efficient photosensitizer is known to lower the amount of UV fluence ($J/m^2$) required for disinfection by orders of magnitude. As shown in FIG. 13, when a photosensitizer is added to a broth containing a mutant strain of $E.$ $Coli,$ the surviving fraction of bacteria for an accumulated fluence is reduced several orders of magnitude. Concurrently the spectral absorbency is wavelength dependent, and can be matched to specific wavelengths. The ability of the photosensitizer to enhance the local absorption of the UV light source near the target material, i.e., cell membranes, cell DNA and RNA, in practice significantly reduces the power, and energy required for the UV light source. The absorption wavelength of the photosensitizer can be matched specifically to the spectral range of the light source to further reduce the fluence and thus the power or energy required for disinfection.

Commercial light sources with a spectral power density at or below 254 nm with an efficiency of better than 25% have been identified. These lamps are specifically matched to the absorption level of hydrogen peroxide. Using the spectral characteristics of this lamp and hydrogen peroxide as a photosensitizer and or ZEROTOL™, indicates that a 100 kW UV source, or array of sources, can reduce $10^9$ CFU/ml of bacteria in one ton of affected material by greater than 7 orders of magnitude in 1000–20000 seconds. Additionally scaling of available data also suggests that other photosensitizers may reduce this power requirement 4–10 times.

Other improvement that may be realized in the process are the following. For the electro-spraying of the sensitizer aerosol, the magnitude and polarity of the embedded charge may be selected to enhance electroporation at the target bacterial cell wall. This allows more rapid transport into the bacterial cell's DNA. Additionally, the magnitude of the charge on the sprayed photosensitizer particles can be tailored to the charge on the bacterial cell wall by adding conductors, semiconductors, and insulating particles to the carrier solvent. The concentration of the photosensitizer can also be selected once the bacterial material, or chemical compound or agent is remotely identified, allowing more rapid disinfection, or neutralization.

The methods and apparatus of the present invention can be used in emergency and military applications to decontaminate vehicles, clothed and unclothed persons, tools and implements, and airborne clouds created by chemical and biological weapons, and industrial accidents. The methods and apparatus of the present invention can also be applied to industrial processes, for example decontaminating circuit boards, work benches and table tops, and industrial tools equipment; food handling and processing equipment; equipment for manufacturing pharmaceuticals and medical devices. The methods and apparatus of the present invention can also be applied to decontaminate foodstuffs, pharmaceutical and pharmaceutical products, and fluids, such as air, water, sewerage, and blood.

From the foregoing description, various modifications and changes in the compositions and method will occur to those skilled in the art without varying from the scope of the invention as defined in the following claims.

What is claimed:

1. A method of decontaminating a cloud containing an aerosol contaminant, the method comprising the steps of:
    applying an aerosol photosensitizer to the cloud; and
    illuminating the cloud to cause chemical reactions to decontaminate the cloud.

2. The method according to claim 1 further comprising electrically charging the aerosol photosensitizer so that it is attracted to the constitute particles of the cloud.

3. The method according to claim 1 when the aerosol photosensitizer is applied to the cloud from an aircraft.

4. The method according to claim 1 wherein the aerosol is applied with a canister.

5. The method according to claim 1 wherein the cloud is illuminated with light having a wave length of between about 200 nm and about 320 nm.

6. The method according to claim 1 wherein the cloud is illuminated with light from an airborne light source.

7. The method according to claim 1 wherein the cloud is illuminated with light from a ground-based light source.

8. The method according to claim 1 wherein the cloud is illuminated with light from a pyrotechnic device.

* * * * *